US012692287B2

(12) United States Patent
Gao et al.

(10) Patent No.: US 12,692,287 B2
(45) Date of Patent: Jul. 28, 2026

(54) POLYMORPHIC FORM OF REDUCED B-NICOTINAMIDE MONONUCLEOTIDE CALCIUM SALT, AND PREPARATION METHOD AND USE THEREFOR

(71) Applicant: EffePharm (Shanghai) Co., Ltd., Shanghai (CN)

(72) Inventors: Xing Gao, Shanghai (CN); Jianjun Yu, Shanghai (CN); Qiang Shen, Shanghai (CN); Qinyuan Xu, Shanghai (CN); Yunkang Ding, Shanghai (CN); Debin Ling, Shanghai (CN); Lulu Xuan, Shanghai (CN); Yang Li, Shanghai (CN); Jialing Liu, Shanghai (CN)

(73) Assignee: EffePharm (Shanghai) Co., Ltd., Shanghai (CN)

( * ) Notice: Subject to any disclaimer, the term of this patent is extended or adjusted under 35 U.S.C. 154(b) by 0 days.

(21) Appl. No.: 19/263,022

(22) Filed: Jul. 8, 2025

(65) Prior Publication Data

US 2025/0388616 A1 Dec. 25, 2025

Related U.S. Application Data

(63) Continuation of application No. PCT/CN2024/094494, filed on May 21, 2024.

(30) Foreign Application Priority Data

Nov. 10, 2023 (CN) ........................ 202311496776.2

(51) Int. Cl.
*C07H 19/048* (2006.01)
*C07H 1/06* (2006.01)

(52) U.S. Cl.
CPC ............ *C07H 19/048* (2013.01); *C07H 1/06* (2013.01)

(58) Field of Classification Search
CPC ...... C07H 1/06; C07H 19/048; C07B 2200/13
See application file for complete search history.

(56) References Cited

U.S. PATENT DOCUMENTS

| | | | |
|---|---|---|---|
| 2025/0361259 | A1 | 11/2025 | Gao et al. |

FOREIGN PATENT DOCUMENTS

| | | | | |
|---|---|---|---|---|
| CN | 108368146 | A | 8/2018 | |
| CN | 111377983 | A | 7/2020 | |
| CN | 113121628 | A | 7/2021 | |
| CN | 113490676 | A | 10/2021 | |
| CN | 115368423 | A | 11/2022 | |
| CN | 116635036 | A | 8/2023 | |
| CN | 119978042 | A | 5/2025 | |
| JP | 2022-158459 | A | 10/2022 | |
| WO | WO 2019/222360 | A1 | 11/2019 | |
| WO | WO 2021/098725 | A1 | 5/2021 | |
| WO | WO 2022/263625 | A1 | 5/2021 | |
| WO | WO-2021214299 | A1 * | 10/2021 | ........... C07D 405/04 |
| WO | WO 2021/230146 | A1 | 11/2021 | |
| WO | WO 2023/160405 | A1 | 8/2023 | |
| WO | WO 2025/097718 | A1 | 5/2025 | |

OTHER PUBLICATIONS

Paulekuhn et al., J. Med. Chem., 2007, 50, p. 6665-6672. (Year: 2007).*
Brittain, H.G., ed., Polymorphism in Pharmaceutical Solids, 1999, Marcel Dekker, Inc., p. 188-194, 202-208, and 219. (Year: 1999).*
Certified copy of the China 202311496776.2 application made available in WIPO application PCT/CN2024/094494, published May 15, 2025. (Year: 2025).*
Ansari et al., "Identification of NAD interacting residues in proteins," BMC bioinformatics, Mar. 10, 2010, 11(1):160, 8 pages.
Cantó et al., "NAD+ metabolism and the control of energy homeostasis: a balancing act between mitochondria and the nucleus," Cell metabolism, Jul. 7, 2015, 22(1):31-53.
Cantó et al., "The NAD+ precursor nicotinamide riboside enhances oxidative metabolism and protects against high-fat diet-induced obesity," Cell metabolism, Jun. 6, 2012, 15(6):838-47.
Chiarugi et al., "The NAD metabolome—a key determinant of cancer cell biology," Nature Reviews Cancer, Sep. 28, 2012, 12(11):741-52.
International Search Report and Written Opinion in International Appln. No. PCT/CN2024/094493, mailed on Jul. 31, 2024, 8 pages (with English translation).
International Search Report and Written Opinion in International Appln. No. PCT/CN2024/094494, mailed on Aug. 5, 2024, 12 pages (with English translation).
Johnson et al., "NAD+ biosynthesis, aging, and disease [version 1; referees: 2 approved]," F1000Research, Feb. 1, 2018, 7:132, 10 pages.
Liu et al., "Engineering the biomimetic cofactors of NMNH for cytochrome P450 BM3 based on binding conformation refinement," RSC advances, 2021, 11(20):12036-42.
Liu et al., "Reduced nicotinamide mononucleotide (NMNH) potently enhances NAD+ and suppresses glycolysis, the TCA cycle, and cell growth," Journal of Proteome Research, Apr. 2021, 20(5):2596-606.
Mills et al., "Long-term administration of nicotinamide mononucleotide mitigates age-associated physiological decline in mice," Cell metabolism, Dec. 13, 2016, 24(6):795-806.

(Continued)

*Primary Examiner* — Jonathan S Lau
(74) *Attorney, Agent, or Firm* — Fish & Richardson P.C.

(57) ABSTRACT

A compound NMNH calcium salt, in particular a polymorph of a reduced β-nicotinamide mononucleotide calcium salt and a preparation method therefor, a use thereof as a pharmaceutical ingredient, a health care product ingredient and a cosmetic ingredient or as a food additive, and a formulation containing same, belonging to the field of medicines, health care products, cosmetics and food additives. For the NMNH calcium salt polymorph, the crystal thereof displays long-term continuous stability, and compared with NMNH disodium salt, has significantly superior stability performance and anti-hygroscopic properties, and is more beneficial to long-term storage, promotion and market application. The NMNH calcium salt crystal is simple in preparation process, easy to control and suitable for large-scale production.

28 Claims, 6 Drawing Sheets

(56) References Cited

OTHER PUBLICATIONS

Office Action in Chinese Appln. No. 202311496776.2, mailed on Jul. 9, 2025, 14 pages (with English translation).
Rajman et al., "Therapeutic potential of NAD-boosting molecules: the in vivo evidence," Cell metabolism, Mar. 6, 2018, 27(3):529-47.
Stein et al., "The dynamic regulation of NAD metabolism in mitochondria," Trends in Endocrinology & Metabolism, Sep. 2012, 23(9):420-8.
Stachurski, "On structure and properties of amorphous materials," Materials, Sep. 15, 2011, 4(9):1564-98.

* cited by examiner

POLYMORPHIC FORM OF REDUCED B-NICOTINAMIDE MONONUCLEOTIDE CALCIUM SALT, AND PREPARATION METHOD AND USE THEREFOR

CROSS REFERENCE TO RELATED APPLICATIONS

This application is a continuation of PCT application No. PCT/CN2024/094494, filed May 21, 2024, which claims priority to CN 202311496776.2 filed Nov. 10, 2023, the contents of each are incorporated by reference herein.

TECHNICAL FIELD

The present invention relates to the field of chemical raw materials for pharmaceuticals, health products, cosmetics, and food additives, specifically to the polymorphic form of reduced β-nicotinamide mononucleotide calcium salt, and a preparation method and a use thereof.

BACKGROUND ART

As one of the most popular molecules in the field of anti-aging, nicotinamide adenine dinucleotide ($NAD^+$) has undoubtedly become the centerpiece of successive anti-aging substances. $NAD^+$ is an essential coenzyme required for over 500 enzymatic reactions and is well-known for its role in oxidation and reduction (Ansari and Raghava, 2010; Rajman et al., 2018; Stein and Imai, 2012). Increasing research indicates that elevating $NAD^+$ levels can significantly improve multi-organ functions, including liver function, kidney function, heart function, and skeletal muscle function (Canto et al., 2012; Mills et al., 2016; Rajman et al., 2018). $NAD^+$ can be synthesized using tryptophan in the de novo biosynthesis pathway, nicotinic acid (NA) in the Preiss-Handler pathway, and nicotinamide (NAM), nicotinamide riboside (NR), and nicotinamide mononucleotide (NMN) in the salvage pathway (Canto et al., 2015; Chiarugi et al., 2012; Johnson and Imai, 2018). In particular, as key intermediates of $NAD^+$, NAM, NR, and NMN have been extensively studied for their potential therapeutic effects in numerous mouse disease models (Mills et al., 2016). Among them, NMN is considered the most suitable NAD+precursor currently, and NMN is experiencing strong global market demand, being highly favored by consumers.

NMNH (molecular structure shown as Formula (A)) has the Chinese name "reduced nicotinamide mononucleotide" or "reduced β-nicotinamide mononucleotide." It is the reduced form of NMN and serves as a novel precursor for $NAD^+$ supplementation, exhibiting superior $NAD^+$-promoting effects compared to NMN, along with other biological functions such as enhancing cellular antioxidant capacity, reducing fat accumulation, decreasing inflammatory responses, and inhibiting tumor cell growth. It is a health-promoting reagent with significant commercial potential (WO2021098725A1).

(A)

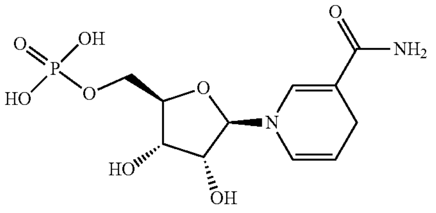

NMNH

NMNH is the reduced form of NMN, sensitive to air, easily oxidized, and unstable, making it unsuitable for long-term storage and market promotion. WO2023160405 (A1) reported the NMNH disodium salt compound and its crystalline and amorphous forms. When exposed in a stability test chamber at 25° C. and 65% RH, the NMNH disodium salt amorphous powder turned into an oil after 1 day, with purity decreasing from 99.30% to 99.02%, while the NMNH disodium salt crystalline Form A solid showed a purity decrease from 99.33% to 99.01% after 5 days. Such stability fails to meet the shelf-life requirements for commercial products, hindering market promotion.

Therefore, there is still an urgent need in the art to develop new NMNH salt forms with improved stability, better suitability for long-term storage, and enhanced market promotion.

SUMMARY OF THE INVENTION

The present invention aims to provide a new salt form of an NMNH compound with better stability, more conducive to long-term storage and market promotion, specifically relating to polymorphs of the reduced form of β-nicotinamide mononucleotide calcium salt, as well as the preparation method and use thereof.

In a first aspect of the present invention, a calcium salt crystal of the reduced form of β-nicotinamide mononucleotide represented by formula (I) is provided, (1)

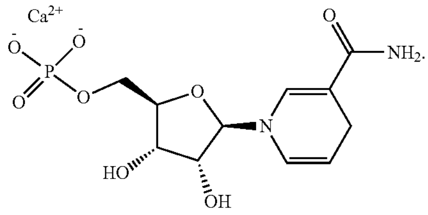

the crystal is selected from the crystalline forms in the group consisting of: crystalline form A, crystalline form B, crystalline form C, crystalline form D, or crystalline form E.

In another preferred embodiment, an XRPD pattern of the crystalline form A comprises 3 or more (e.g., 4, 5, 6, 7, or 8) 2θ values selected from the group consisting of: 6.9°±0.2°, 9.5°±0.2°, 12.6°±0.2°, 15.6°±0.2°, 17.9°±0.2°, 21.0°±0.2°, 21.8°±0.2°, and 25.4°±0.2°;

an XRPD pattern of the crystalline form B comprises 3 or more (e.g., 4, 5, 6, 7, or 8) 2θ values selected from the group consisting of: 6.5°±0.2°, 8.1°±0.2°, 11.9°±0.2°, 13.1°±0.2°, 17.6°±0.2°, 21.4°±0.2°, 23.7°±0.2°, and 26.9°±0.2°;

an XRPD pattern of the crystalline form C comprises 3 or more (e.g., 4, 5, 6, 7, or 8) 2θ values selected from the group consisting of: 6.2°±0.2°, 9.7°±0.2°, 12.4°±0.2°, 16.1°±0.2°, 17.1°±0.2°, 18.7°±0.2°, 20.8°±0.2°, and 26.6°±0.2°.

In another preferred embodiment, the crystal of the reduced form of β-nicotinamide mononucleotide calcium salt is a hydrate, solvate, or organic solvent-hydrate.

In another preferred embodiment, the organic solvent-hydrate of the reduced form of β-nicotinamide mononucleotide calcium salt is an ethanol-hydrate or acetone-hydrate.

In another preferred embodiment, the structural formula of the reduced form of β-nicotinamide mononucleotide calcium salt is as shown in Formula II:

(II)

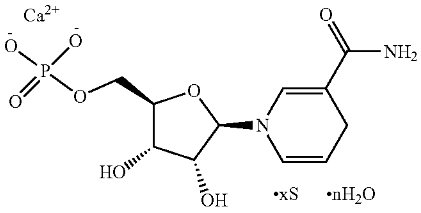

In the above formula, S represents an organic solvent, $H_2O$ is water; when x=0, n>0, it is a hydrate; when x>0, n=0, it is an organic solvate; when x>0, n>0, it is an organic solvent-hydrate.

In another preferred embodiment, x and/or n are independently an integer or a non-integer.

In another preferred embodiment, the crystalline form A further has one or more characteristics selected from the group consisting of:

1) an XRPD pattern of the crystalline form A comprises 6 or more 2θ values selected from the group consisting of: 6.9°±0.2°, 9.5°±0.2°, 12.6°±0.2°, 13.9°±0.2°, 14.4°±0.2°, 15.6°±0.2°, 16.7°±0.2°, 17.2°±0.2°, 17.9°±0.2°, 18.8°±0.2°, 21.0°±0.2°, 21.8°±0.2°, 23.1°±0.2°, 25.4°±0.2°, 26.5°±0.2°, 27.3°±0.2°, 28.1°±0.2°, 31.5°±0.2°, 32.8°±0.2°, and 35.6°±0.2°;
2) the XRPD pattern of the crystalline form A is substantially characterized as shown in FIG. 1;
3) the crystalline form A is a hydrate with a water content of 4% wt to 13% wt; and preferably, the crystalline form A is a monohydrate to trihydrate.

In another preferred embodiment, the crystalline form A is a hydrate with a water content of 5% wt-12% wt.

In another preferred embodiment, the crystalline form A is a hydrate with a water content of 6% wt-11% wt.

In another preferred embodiment, the crystalline form B further has one or more characteristics selected from the group consisting of:

1) an XRPD pattern of the crystalline form B comprises 6 or more 2θ values selected from the group consisting of: 6.5°±0.2°, 8.1°±0.2°, 11.9°±0.2°, 13.1°±0.2°, 13.5°±0.2°, 14.5°±0.2°, 17.6°±0.2°, 18.0°±0.2°, 18.9°±0.2°, 19.4°±0.2°, 19.7°±0.2°, 20.3°±0.2°, 21.4°±0.2°23.7°±0.2°, 24.3°±0.2°, 25.1°±0.2°, 26.4°±0.2°, 26.9°±0.2°, 27.5°±0.2°, 28.7°±0.2°, 29.3°±0.2°, 30.5°±0.2°, 30.9°±0.2°, 31.6°±0.2°, 32.4°±0.2°, 32.9°±0.2°, 34.2°±0.2°, 35.0°±0.2°, 35.4°±0.2°, 36.7°±0.2°, 37.5°±0.2°, 37.9°±0.2°, 38.2°±0.2°, 38.9°±0.2°, and 40.2°±0.2°;
2) the XRPD pattern of the crystalline form B is substantially characterized as shown in FIG. 2;
3) the crystalline form B is a hydrate with a water content of 4% wt to 20% wt; and preferably, the crystalline form B is a monohydrate to pentahydrate.

In another preferred embodiment, the crystalline form B is a hydrate with a water content of 5% wt-19% wt.

In another preferred embodiment, the crystalline form B is a hydrate with a water content of 6% wt-18% wt.

In another preferred embodiment, the crystalline form C further has one or more characteristics selected from the group consisting of:

1) an XRPD pattern of the crystalline form C comprises 6 or more 2θ values selected from the group consisting of: 6.2°±0.2°, 6.8°±0.2°, 9.7°±0.2°, 11.8°±0.2°, 12.4°±0.2°, 14.2°±0.2°, 15.5°±0.2°, 16.1°±0.2°, 17.1°±0.2°, 17.9°±0.2°, 18.7°±0.2°, 20.1°±0.2°, 20.8°±0.2°, 21.5°±0.2°, 22.9°±0.2°, 23.5°±0.2°, 24.1°±0.2°, 24.5°±0.2°, 25.0°±0.2°, 25.8°±0.2°, 26.6°±0.2°27.3°±0.2°, 27.7°±0.2°, 28.3°±0.2°, 28.5°±0.2°, 29.7°±0.2°, 30.3°±0.2°, 30.8°±0.2°, 31.4°±0.2°, 32.8°±0.2°, 33.4°±0.2°, 34.4°±0.2°, 35.3°±0.2°, 36.0°±0.2°, 37.1°±0.2°, 38.0°±0.2°, 39.0°±0.2°, and 39.8°±0.2°;
2) the XRPD pattern of the crystalline form C is substantially characterized as shown in FIG. 3;
3) the crystalline form C is a hydrate with a water content of 4% wt to 13% wt; and preferably, the crystalline form C is a monohydrate to trihydrate.

In another preferred embodiment, the crystalline form C is a hydrate with a moisture content of 5% wt-12% wt.

In another preferred embodiment, the crystalline form C is a hydrate with a moisture content of 6% wt-11% wt.

In another preferred embodiment, the crystalline form D has one or more characteristics selected from the group consisting of:

1) an XRPD pattern of the crystalline form D comprises 3 or more 2θ values selected from the group consisting of: 7.0°±0.2°, 8.0°±0.2°, 12.0°±0.2°, 17.8°±0.2°, 20.2°±0.2°, 26.9°±0.2°;
2) the XRPD pattern of the crystalline form D further comprises 1 or more 2θ values selected from the group consisting of: 13.5°±0.2°, 14.2°±0.2°, 24.0°±0.2°;
3) the XRPD pattern of the crystalline form D comprises 6 or more 2θ values selected from the group consisting of: 7.0°±0.2°, 8.0°±0.2°, 12.0°±0.2°, 13.5°±0.2°, 14.2°±0.2°, 15.7°±0.2°, 17.8°±0.2°, 19.2°±0.2°, 20.2°±0.2°, 23.5°±0.2°, 24.0°±0.2°, 24.5°±0.2°, 26.1°±0.2°, 26.9°±0.2°, 28.7°±0.2°, 30.5°±0.2°, 33.8°±0.2°;
4) the XRPD pattern of the crystalline form D is substantially characterized as shown in FIG. 4;
5) a $^1H$ NMR spectrum of the crystalline form D is substantially characterized as shown in FIG. 7;
6) the crystalline form D is an ethanol hydrate, containing about 0.2-0.5 ethanol molecules, with a water content of 16% wt-23% wt; and preferably, the crystalline form D is a trihydrate to hexahydrate.

In another preferred embodiment, the crystalline form D is an ethanol-hydrate with a moisture content of 18% wt-21% wt.

In another preferred embodiment, the crystalline form E has one or more characteristics selected from the group consisting of:

1) an XRPD pattern of the crystalline form E comprises 3 or more 2θ values selected from the group consisting of: 6.9°±0.2°, 8.0°±0.2°, 11.9°±0.2°, 17.8°±0.2°, 20.2°±0.2°, 26.9°±0.2°;
2) the XRPD pattern of the crystalline form E further comprises 1 or more 2θ values selected from the group consisting of: 13.5°±0.2°, 14.2°±0.2°, 24.0°±0.2°;
3) the XRPD pattern of the crystalline form E comprises 6 or more 2θ values selected from the group consisting of: 6.9°±0.2°, 8.0°±0.2°, 11.9°±0.2°, 13.5°±0.2°, 14.2°±0.2°, 15.7°±0.2°, 17.8°±0.2°, 18.8°±0.2°, 19.2°±0.2°, 20.2°±0.2°, 24.1°±0.2°, 26.0°±0.2°, 26.9°±0.2°, 28.7°±0.2°, 30.7°±0.2°, 33.9°±0.2°;
4) the XRPD pattern of the crystalline form E is substantially characterized as shown in FIG. 5;

5) a $^1$H NMR spectrum of the crystalline form D is substantially characterized as shown in FIG. 8;

6) the crystalline form E is an acetone hydrate, containing about 0.2-0.5 acetone molecules, with a water content of 16% wt-23% wt; and preferably, the crystalline form E is a trihydrate to hexahydrate.

In another preferred embodiment, the crystalline form E is an acetone-hydrate with a moisture content of 18% wt-21% wt.

In a second aspect of the present invention, there is provided a method for preparing the crystal as set forth in the first aspect, the method comprises the following steps:

(I) Preparation of the crystalline form A:

I-1) providing a solution containing a reduced β-nicotinamide mononucleotide calcium salt formed in a first solvent;

I-2) at 40-50° C., dropwise adding a second solvent into the solution of the reduced β-nicotinamide mononucleotide calcium salt set forth in step I-1), crystallizing, filtering and drying at 40-50° C. to obtain the crystalline form A of the reduced β-nicotinamide mononucleotide calcium salt, wherein the first solvent is selected from: water; the second solvent is selected from: water, methanol, ethanol, n-propanol, isopropanol, acetone, acetonitrile, tetrahydrofuran, or a mixed solvent thereof;

(II) Preparation of the crystalline form B:

II-1) providing a solution containing the reduced β-nicotinamide mononucleotide calcium salt formed in a first solvent;

II-2) at 20-30° C., dropwise adding a second solvent into the solution of the reduced β-nicotinamide mononucleotide calcium salt set forth in step II-1), crystallizing, filtering and drying at 20-30° C. to obtain the crystalline form B of the reduced β-nicotinamide mononucleotide calcium salt, wherein the first solvent is selected from: water; the second solvent is selected from: water, methanol, or a mixed solvent thereof;

(III) Preparation of the crystalline form C:

III-1) providing a solution containing the reduced β-nicotinamide mononucleotide calcium salt formed in a first solvent;

III-2) at 20-30° C., dropwise adding a second solvent into the solution of the reduced β-nicotinamide mononucleotide calcium salt set forth in step III), crystallizing, filtering, and then drying at 40-50° C. to obtain the crystalline form C of the reduced β-nicotinamide mononucleotide calcium salt, wherein the first solvent is selected from: water; the second solvent is selected from: water, methanol, or a mixed solvent thereof;

(IV) Preparation of the crystalline form D:

IV-1) providing a solution containing the reduced β-nicotinamide mononucleotide calcium salt formed in a first solvent;

IV-2) at 20-30° C., dropwise adding a second solvent into the solution of the reduced β-nicotinamide mononucleotide calcium salt set forth in step IV-1), crystallizing, filtering, and then drying at 30-40° C. to obtain the crystalline form D of the reduced β-nicotinamide mononucleotide calcium salt, wherein the first solvent is selected from: water; the second solvent is selected from: water, ethanol, or a mixed solvent thereof;

(V) Preparation of the crystalline form E:

V-1) providing a solution containing the reduced β-nicotinamide mononucleotide calcium salt formed in a first solvent;

V-2) at 20-30° C., dropwise adding a second solvent into the solution of the reduced β-nicotinamide mononucleotide calcium salt set forth in step V-1), crystallizing, filtering, and then drying at 30-40° C. to obtain the crystalline form E of the reduced β-nicotinamide mononucleotide calcium salt, wherein the first solvent is selected from: water; the second solvent is selected from: water, acetone, or a mixed solvent thereof.

In another preferred embodiment, the solution containing the reduced form β-nicotinamide mononucleotide calcium salt is provided by the following method: adding the reduced form β-nicotinamide mononucleotide calcium salt to a first solvent to obtain a solution containing the reduced form β-nicotinamide mononucleotide calcium salt, or generating the reduced form β-nicotinamide mononucleotide calcium salt solution in situ in a reaction solution.

In another preferred embodiment, the preparation method of the crystalline form comprises the following steps:

1) Providing a solution of reduced form β-nicotinamide mononucleotide calcium salt formed in a first solvent;

2) Under stirring conditions, adding a second solvent dropwise to the reduced form β-nicotinamide mononucleotide calcium salt solution described in step 1), and crystallizing to obtain crystals of reduced form β-nicotinamide mononucleotide calcium salt.

In another preferred embodiment, the first solvent and the second solvent are the same or different, and are independently selected from the group consisting of: water, acetonitrile, tetrahydrofuran, methyl tert-butyl ether, 2-methyltetrahydrofuran, dichloromethane, N,N-dimethylformamide, N,N-dimethylacetamide, N,N-diethylformamide, dimethyl sulfoxide, ethyl acetate, isopropyl acetate, ketone solvents, alcohol solvents, or combinations thereof.

In another preferred embodiment, the ketone solvent is selected from the group consisting of: acetone, 2-butanone, methyl isobutyl ketone, methyl tert-butyl ketone, 3-methyl-2-butanone, or combinations thereof.

In another preferred embodiment, the alcohol solvent is selected from the group consisting of: methanol, ethanol, n-propanol, isopropanol, n-butanol, isobutanol, n-pentanol, or combinations thereof.

In a third aspect of the present invention, a composition is provided, the composition comprises: (a) the crystal according to the first aspect, and (b) a pharmaceutically acceptable excipient or carrier, or a health product acceptable excipient or carrier, or a cosmetically acceptable excipient or carrier, or a food acceptable excipient or carrier.

In another preferred embodiment, the composition is selected from the group consisting of: a pharmaceutical composition, a health product composition, a cosmetic composition, or a food composition.

In another preferred embodiment, the pharmaceutical composition comprises: (a) any crystal as set forth in the first aspect, and (b) a pharmaceutically acceptable excipient or carrier.

In another preferred embodiment, the dosage form of the pharmaceutical composition is selected from the group consisting of: oral formulation, injectable formulation, respiratory administration formulation, dermal administration formulation, mucosal administration formulation, cavity administration formulation, and the like.

In another preferred embodiment, the health product composition comprises: (a) any crystal as set forth in the first aspect, and (b) an excipient or carrier acceptable for health products.

In another preferred embodiment, the cosmetic composition comprises: (a) any crystal as set forth in the first aspect, and (b) an excipient or carrier acceptable for cosmetics.

In another preferred embodiment, the cosmetic composition comprises cosmetics used for purposes selected from the group consisting of: skin cosmetics, hair cosmetics, beauty cosmetics, and special function cosmetics.

In another preferred embodiment, the food composition comprises: (a) any crystal as set forth in the first aspect, and (b) an excipient or carrier acceptable for food.

In a fourth aspect of the present invention, a use of the crystal as set forth in the first aspect for the preparation of a medicament, a health product, a cosmetic or a food additive is provided.

In another preferred embodiment, the drug is used to protect the optic nerve, improve retinal damage, prevent/treat hair loss, prevent/improve cardiovascular and cerebrovascular diseases, inhibit renal tubular damage and aging, prevent liver fibrosis, improve fatty liver disease, alleviate dry eye symptoms, repair kidney damage, prevent diabetes/nephropathy, improve sarcopenia symptoms in the elderly, treat chronic inflammation, alleviate the condition of patients with polycystic ovary syndrome, prevent/delay glaucoma, reduce neuroinflammation, mitigate the cardiac toxicity of anthracycline chemotherapeutic drugs, aid in stroke recovery, and prevent/treat heart failure in the elderly.

In another preferred embodiment, the health supplement is used to slow cellular aging, delay female reproductive aging, enhance fertility, improve menopausal symptoms, enhance male sexual function, improve sleep, soothe emotions, boost energy, improve cardiovascular function, enhance cardiovascular health, boost immunity, improve sub-health conditions, prevent tumors, and prevent Alzheimer's disease.

In another preferred embodiment, the cosmetic is used to improve damaged cell function, enhance skin/hair quality, prevent/treat skin photoaging, maintain skin softness and elasticity, and delay skin aging.

In another preferred embodiment, the food additive is used to improve appetite, enhance digestive function, promote metabolism, promote hair/nail growth, and enhance nutritional value.

It should be understood that within the scope of the present invention, the above technical features of the present invention and the technical features specifically described below (e.g., in the embodiments) can be combined with each other to form new or preferred technical solutions. Due to space limitations, they are not exhaustively listed herein.

DESCRIPTION OF THE EMBODIMENTS

Figure 1:
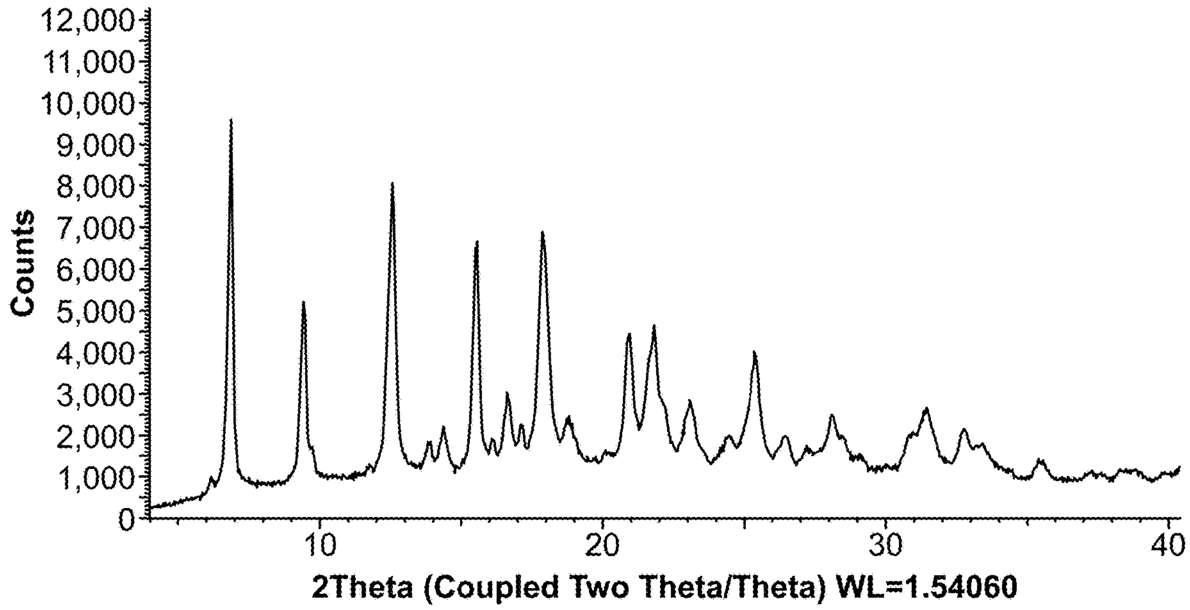
FIG. 1 shows an XRPD pattern of NMNH calcium salt crystalline form A.

Through extensive and in-depth research, the inventors have unexpectedly developed a specific salt of NMNH for the first time, the salt can be NMNH calcium salt. The studies of the present invention show that the polymorphs of NMNH calcium salt exhibit excellent stability. Compared with the crystalline form and amorphous form of NMNH disodium salt, the polymorphs of NMNH calcium salt (crystalline forms A, B, C, D, and E) demonstrate long-term sustained stability and resistance to moisture absorption, making them more suitable for long-term storage and market promotion. Furthermore, the polymorphs of the present invention meet the shelf-life requirements for commercial products and are suitable for use in pharmaceutical compositions, health supplements, cosmetics, food additives, and the like. On this basis, the inventors have completed the present invention.

Terminology

Unless otherwise defined, all technical and scientific terms used herein have the same meaning as commonly understood by a person of ordinary skill in the art to which the present invention belongs.

As used herein, the term "n$H_2O$" refers to n as encompassing all possible values between 0 and 6, including integers and non-integers; "$H_2O$" is the chemical formula for water, representing water molecules or water. The x in "xS" refers to all possible values between 0 and 6, including integers and non-integers; "S" herein refers to organic solvent molecules, which can be any type of organic solvent.

As used herein, when referring to, for specifically listed numerical values, the term "about" means that the value may vary from the listed specific value by no more than 1%. For example, as used herein, the expression "about 100" includes all values between 99 and 101 (e.g., 99.1, 99.2, 99.3, 99.4, etc.).

As used herein, the term "containing" or "including (comprising)" may be open-ended, semi-closed, or closed. In other words, the term also includes "substantially composed of" or "composed of."

As used herein, the term "n or more 2θ values selected from the group" refers to n and any positive integer greater than n (e.g., n, n+1, . . . ), where the upper limit Nup is the total number of 2θ peaks in the group. For example, "3 or more" includes not only the positive integers 3, 4, 5, 6, 7, 8, 9, 10, 11, 12, 13, 14, 15, 16, 17, 18, 19, 20, 21, . . . up to the upper limit Nup, but also ranges such as "4 or more," "5 or more," "6 or more," and so forth.

NMNH Calcium Salt

As used herein, the terms "reduced β-nicotinamide mononucleotide calcium salt," "β-dihydronicotinamide mononucleotide calcium salt," "dihydronicotinamide mononucleotide calcium salt," "reduced nicotinamide mononucleotide calcium salt," "reduced NMN calcium salt," "NMNH calcium salt," and "NMNH-Ca" are used interchangeably and all refer to the salt formed by reduced β-nicotinamide mononucleotide and calcium ions, with the structure shown in Formula (I). It should be understood that this term comprises amorphous forms, hydrates, solvates, solvate-hydrates, and anhydrates.

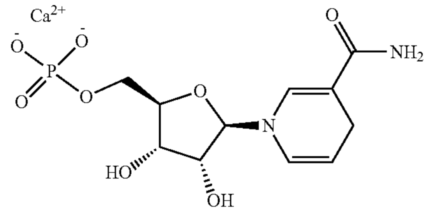

(I)

In the present invention, the preferred reduced form NMNH calcium salt is a hydrate, with a structure as shown in Formula (II):

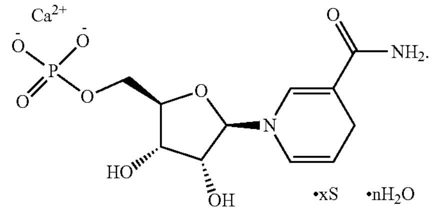

(II)

Polymorphs

Solids exist either in an amorphous form or in a crystalline form. In the case of a crystalline form, molecules are positioned within a three-dimensional lattice. When a compound crystallizes from a solution or slurry, it can crystallize with different spatial lattice arrangements (a property referred to as "polymorphism"), forming crystals with different crystalline forms, and these various crystalline forms are called "polymorphs." Different polymorphs of a given substance may differ from each other in one or more physical properties (such as solubility and dissolution rate, true specific gravity, crystal shape, packing behavior, flowability, and/or solid-state stability).

The polymorphic forms of a compound may exhibit different melting points, hygroscopicity, stability, solubility, bioavailability, bioactivity, and flowability, which can be important factors affecting druggability.

As used herein, the terms "crystal," "crystal of the present invention," or "polymorph" are used interchangeably and refer to the crystal described in the first aspect of the present invention, with a crystalline form selected from the group consisting of: crystalline form A, crystalline form B, crystalline form C, crystalline form D, or crystalline form E.

Crystallization

Production-scale crystallization can be achieved by manipulating a solution so that the solubility limit of the target compound is exceeded. This can be accomplished in various ways, for example, by dissolving the compound at a relatively high temperature and then cooling the solution below the saturation limit. Alternatively, it can be done by boiling, atmospheric evaporation, vacuum drying, or by other methods to reduce the volume of the liquid. The solubility of the target compound can also be reduced by adding an antisolvent or a solvent or a mixture of such solvents in which the compound has low solubility. Another alternative method is to adjust the pH value to reduce solubility. For a detailed description of crystallization, see Crystallization, 3rd Edition, J.W. Mullens, Butterworth-Heinemann Ltd., 1993, ISBN 0750611294.

If it is desired that salt formation and crystallization occur simultaneously, and if the salt has lower solubility in the reaction medium than the starting materials, then the addition of an appropriate acid or base can lead to direct crystallization of the desired salt. Similarly, in a medium in which the final desired form has lower solubility than the reactants, completion of the synthesis reaction can result in direct crystallization of the final product.

Crystallization optimization may include seeding the crystallization medium with crystals of the desired form. Additionally, many crystallization methods employ a combination of the above strategies. One implementation involves dissolving the target compound in a solvent at high temperature, followed by controlled addition of an appropriate volume of antisolvent such that the system is just below the saturation level. At this point, seed crystals of the desired form may be added (while maintaining the integrity of the seed crystals), and the system is cooled to complete crystallization.

Solvates

During the contact process between a compound or drug molecule and solvent molecules, it is difficult to avoid the situation where external and internal factors cause the solvent molecules to form a cocrystal with the compound molecules and remain in the solid substance. The substance formed after the compound and the solvent crystallize is called a solvate. Types of solvents that readily form solvates with organic compounds include water, methanol, ethanol, benzene, ether, heterocyclic aromatic hydrocarbons, etc.

Hydrates

A hydrate is a special type of solvate. In the pharmaceutical industry, whether in the synthesis of active pharmaceutical ingredients, pharmaceutical formulations, drug storage, or drug activity evaluation, hydrates have unique characteristics that merit separate discussion.

In the present invention, the crystal of the compound represented by formula (I) can be a non-solvate or a solvate; the crystalline forms A, B, and C of the compound represented by formula (I) are all hydrates, crystalline form D is an ethanol-hydrate, and crystalline form E is an acetone-hydrate.

Uses

The present invention provides the uses of NMNH calcium salt crystals (including crystalline forms A, B, C, D, and E): the crystals are highly efficient and broad-spectrum, and can be used in pharmaceutical compositions, health products, cosmetics, food additives, etc.

Compared with the Existing Technology, the Beneficial Effects of the Present Invention are as Follows:

(1) The crystal of the compound of formula (I) of the present invention (including crystalline forms A, B, C, D, and E), compared with the NMNH disodium salt crystalline form and amorphous solid, has better stability, lower hygroscopicity, and is more suitable for long-term storage and market promotion.

(2) The crystal of the compound of formula (I) of the present invention (including crystalline forms A, B, C, D, and E) has a simple preparation method and is suitable for industrial production.

(3) The crystal of the compound of formula (I) of the present invention (including crystalline forms A, B, C, D, and E) can be used in pharmaceutical compositions, health products, cosmetics, food additives, etc.

The present invention is further described below in conjunction with specific examples. It should be understood that these examples are only used to illustrate the present invention, and are not intended to limit the scope of the present invention. The experimental methods in the following examples, for which specific conditions are not specified, are generally conducted under conventional conditions or according to the conditions recommended by the manufacturer. Unless otherwise stated, percentages and parts are by weight.

Unless otherwise defined, all professional and scientific terms used herein have the same meaning as those familiar to a person skilled in the art. Furthermore, any methods and materials similar or equivalent to those described herein can be applied to the methods of the present invention.

Test Methods

XRPD (X-ray Powder Diffraction) Pattern Determination Method: Bruker D2 Phaser X-ray Powder Diffractometer; Radiation Source Cu (1.54060 Å).

Measurement variations associated with the results of this type of X-ray powder diffraction Asc diffraction analysis arise from several factors, including: (a) errors in sample preparation (e.g., sample height), (b) instrument errors, (c) calibration differences, (d) operator errors (including those occurring during peak position determination), and (e) material properties (e.g., preferred orientation errors). Calibration errors and sample height errors often lead to displacement of all peaks in the same direction. When using a flat holder, small differences in sample height can lead to significant displacement in XRPD peak positions. Systematic studies show that a 1 mm difference in sample height can result in a peak shift of up to 1° in 2θ. These displacements can be identified from the XRPD pattern and can be corrected by compensating for the displacement (applying a systematic calibration factor to all peak position values) or by recalibrating the instrument. As mentioned above, by applying a systematic calibration factor to align peak positions, measurement errors from different instruments can be corrected.

The following examples provide description of the present invention without limiting the present invention.

Example 1. Preparation of NMNH Calcium Salt Aqueous Solution

To 10 liters of saturated sodium bicarbonate aqueous solution, 1.7 kg of β-NMN and 0.94 kg of sodium dithionite were added, stirred at room temperature overnight, and filtered to obtain a clear solution. The pH of the clear solution was adjusted to 3-4 with 37% hydrochloric acid. The solution was desalted using electrodialysis until the conductivity of the solution decreased to 50-100 μS. The pH of the solution was adjusted to 10 with calcium hydroxide; alternatively, 0.57 kg of calcium chloride was added, and the pH was adjusted to 10 with sodium hydroxide. An NMNH calcium salt aqueous solution was obtained, containing approximately 1.71 kg of NMNH calcium salt (solution purity determined by HPLC to be 94.5%).

Example 2. Preparation of NMNH Calcium Salt Crystalline Form A 500 ml of NMNH calcium salt aqueous solution was stirred in an oil bath at 40-50° C. 2 L of methanol was slowly added dropwise over more than 1 hour. After the addition was complete, the mixture was stirred at 40-50° C. for 1-2 hours, then filtered and dried at 40-50° C. to obtain 79.5 g of NMNH calcium salt crystal. The obtained crystal was crystalline form A, with a yield of 84.2% and a purity of 99.83%.

Figure 6:
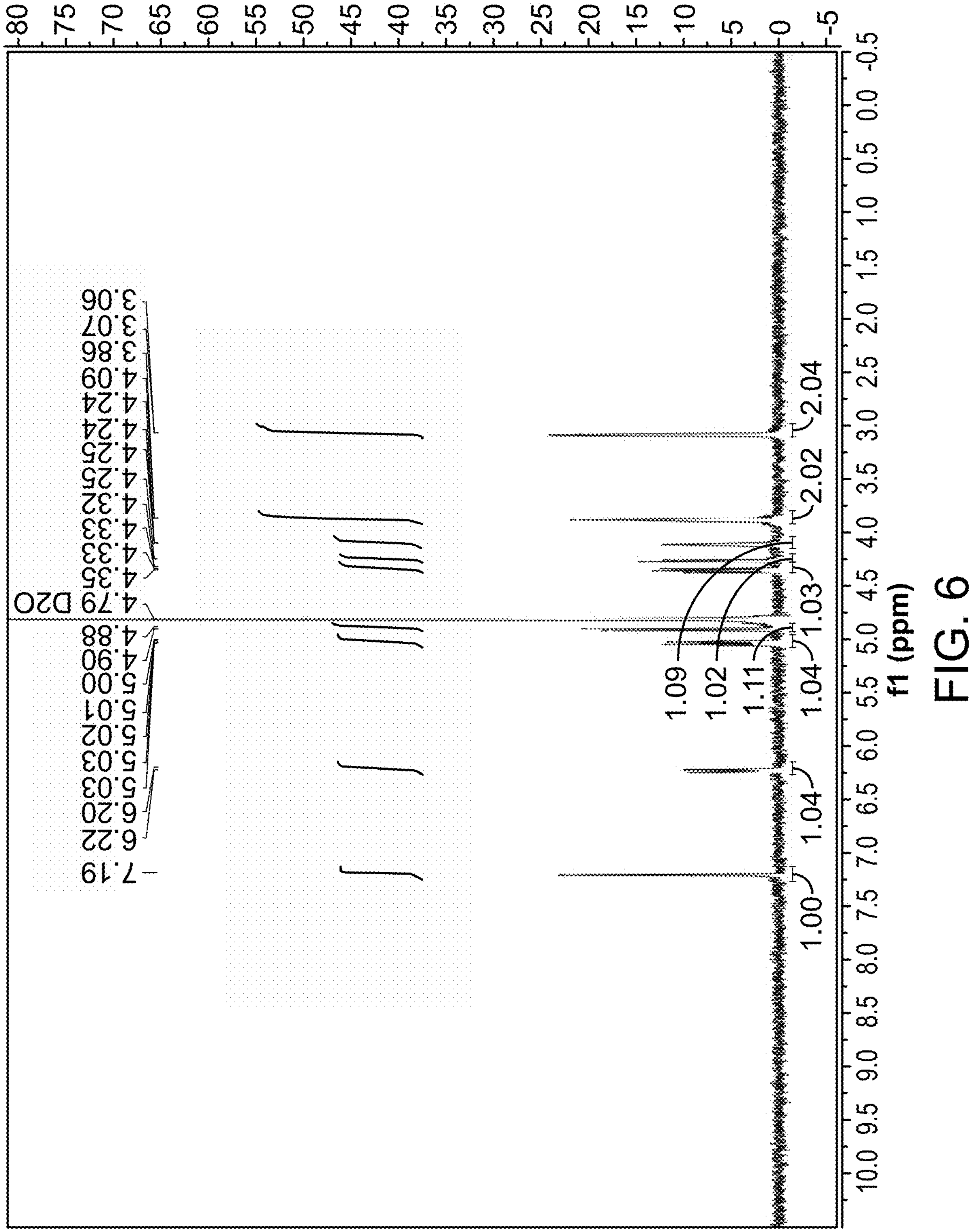
FIG. 6 shows a $^1$H NMR spectrum of NMNH calcium salt hydrate crystalline forms A, B, and C.

The obtained solid was subjected to X-ray powder diffraction testing. The XRPD pattern of crystalline form A was basically as shown in FIG. 1, and the $^{1}H$ NMR spectrum was as shown in FIG. 6. The diffraction angle data were basically as shown in Table 1 below, in which the error range of the 2θ values was ±0.2°. The crystalline form A was a hydrate with a water content of 9.2% wt.

TABLE 1

XRPD Data of crystalline form A

| 2θ (°) | d (Å) | Relative intensity |
|---|---|---|
| 6.90 | 12.80798 | 100.00% |
| 9.45 | 9.35343 | 51.60% |
| 12.59 | 7.02725 | 83.20% |
| 13.91 | 6.36349 | 8.50% |
| 14.37 | 6.15884 | 12.10% |
| 15.58 | 5.685 | 63.80% |
| 16.65 | 5.32022 | 22.00% |
| 17.15 | 5.16509 | 11.30% |
| 17.90 | 4.95114 | 67.40% |
| 18.81 | 4.71318 | 13.10% |
| 20.96 | 4.23497 | 36.80% |
| 21.83 | 4.06741 | 39.90% |
| 23.09 | 3.84858 | 17.60% |
| 25.40 | 3.5039 | 32.40% |
| 26.46 | 3.3656 | 7.30% |
| 27.25 | 3.26985 | 4.50% |
| 28.12 | 3.1712 | 14.30% |
| 31.45 | 2.84246 | 17.80% |
| 32.79 | 2.72933 | 12.70% |
| 35.55 | 2.52322 | 7.30% |

Example 3. Preparation of NMNH Calcium Salt Crystalline Form B 500 ml of NMNH calcium salt aqueous solution was stirred in a 20-30° C. oil bath, 2 L of methanol was added at one time, stirred at 20-30° C. for 1-2 hours, filtered, and dried at 20-30° C. to obtain 80.3 g of NMNH calcium salt crystals. The obtained crystals were of crystalline form B, with a yield of 85.0% and a purity of 99.75%.

Figure 2:
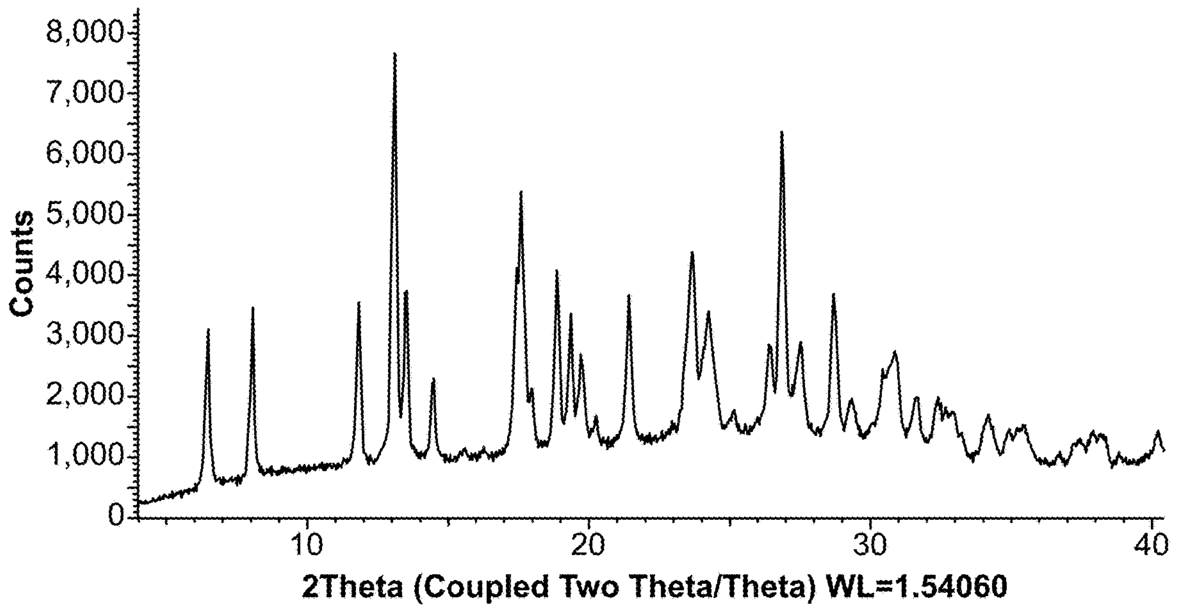
FIG. 2 shows an XRPD pattern of NMNH calcium salt crystalline form B.

The obtained solid was subjected to X-ray powder diffraction testing. The XRPD pattern of crystalline form B obtained was basically as shown in FIG. 2, the $^{1}H$ NMR spectrum as shown in FIG. 6, and the diffraction angle data were basically as shown in Table 2 below, with an error range of ±0.2° for the 2θ values. The crystalline form B is a hydrate with a water content of 13.3% wt.

TABLE 2

| XRPD data of crystalline form B | | |
|---|---|---|
| 2θ (°) | d (Å) | Relative intensity |
| 6.50 | 13.59751 | 35.00% |
| 8.07 | 10.9422 | 39.50% |
| 11.85 | 7.46152 | 39.10% |
| 13.11 | 6.74933 | 100.00% |
| 13.50 | 6.55221 | 41.30% |
| 14.47 | 6.11638 | 19.00% |
| 17.61 | 5.03257 | 64.10% |
| 17.98 | 4.93053 | 14.90% |
| 18.89 | 4.69536 | 43.50% |
| 19.36 | 4.58022 | 31.90% |
| 19.73 | 4.49611 | 20.90% |
| 20.26 | 4.37951 | 7.20% |
| 21.44 | 4.14153 | 35.50% |
| 23.66 | 3.75698 | 44.60% |
| 24.25 | 3.66758 | 30.60% |
| 25.10 | 3.54465 | 5.40% |
| 26.44 | 3.36895 | 21.40% |
| 26.87 | 3.31547 | 76.20% |
| 27.51 | 3.23951 | 21.90% |
| 28.70 | 3.1082 | 36.80% |
| 29.32 | 3.0434 | 7.50% |
| 30.46 | 2.9327 | 17.50% |
| 30.87 | 2.8947 | 22.40% |
| 31.63 | 2.82611 | 11.00% |
| 32.39 | 2.76185 | 12.60% |
| 32.86 | 2.7238 | 9.90% |
| 34.16 | 2.62238 | 10.90% |
| 34.96 | 2.5646 | 5.00% |
| 35.41 | 2.53291 | 8.80% |
| 36.73 | 2.44482 | 2.50% |
| 37.48 | 2.39762 | 4.70% |
| 37.92 | 2.37114 | 7.70% |
| 38.18 | 2.3551 | 7.00% |
| 38.85 | 2.31647 | 2.10% |
| 40.21 | 2.24087 | 5.80% |

Example 4. Preparation of NMNH Calcium Salt Crystalline Form C 500 ml of NMNH calcium salt aqueous solution was stirred in a 20-30° C. oil bath, and 2 L of methanol was slowly added dropwise, with the dropping time being more than 1 hour. After the addition was complete, stirring was continued for 1-2 hours, filtered, and dried at 40-50° C. to obtain 80.1 g of NMNH calcium salt crystals. The obtained crystals were crystalline form C, with a yield of 84.8% and a purity of 99.78%.

Figure 3:
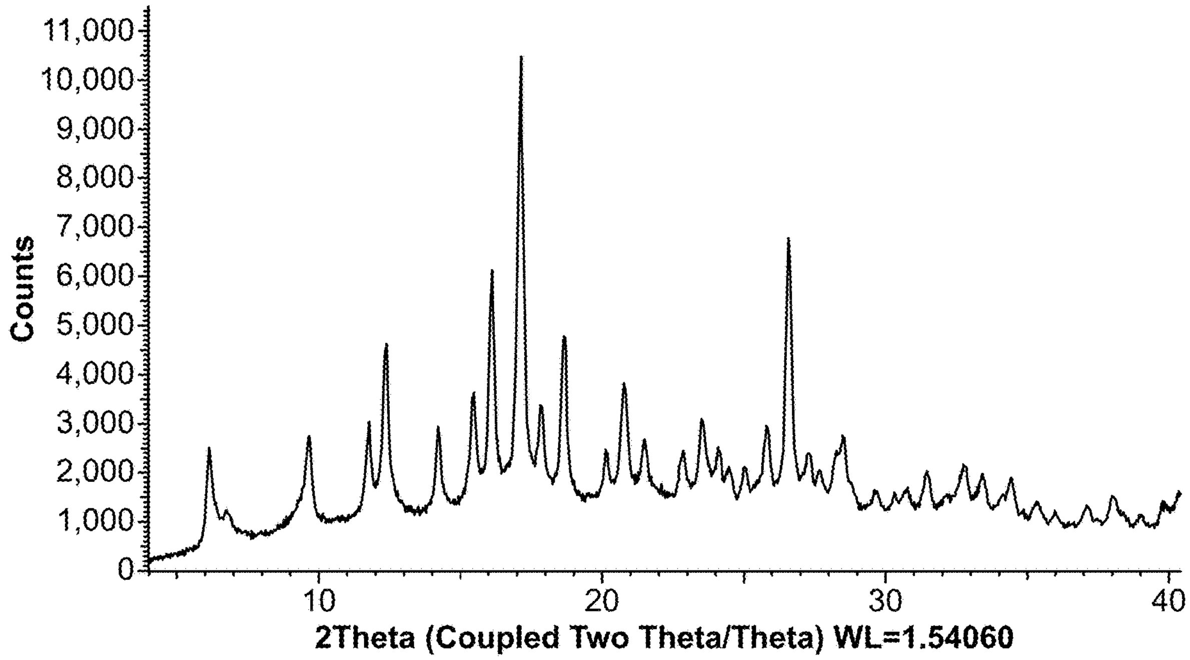
FIG. 3 shows an XRPD pattern of NMNH calcium salt crystalline form C.

The obtained solid was subjected to X-ray powder diffraction testing. The XRPD pattern of crystalline form C obtained was basically as shown in FIG. 3, the $^{1}H$ NMR spectrum as shown in FIG. 6, and the diffraction angle data were basically as shown in Table 3 below, with an error range of ±0.2° for the 2θ values. The crystalline form C is a hydrate with a water content of 9.5% wt.

TABLE 3

| XRPD data of crystalline form C | | |
|---|---|---|
| 2θ (°) | d (Å) | Relative intensity |
| 6.15 | 14.36193 | 19.80% |
| 6.76 | 13.05853 | 6.10% |
| 9.66 | 9.14804 | 19.80% |
| 11.76 | 7.51895 | 21.10% |
| 12.38 | 7.14644 | 38.10% |
| 14.20 | 6.2303 | 19.00% |
| 15.48 | 5.72149 | 24.60% |
| 16.12 | 5.49534 | 51.70% |

TABLE 3-continued

| XRPD data of crystalline form C | | |
|---|---|---|
| 2θ (°) | d (Å) | Relative intensity |
| 17.14 | 5.17059 | 100.00% |
| 17.85 | 4.96625 | 20.90% |
| 18.66 | 4.75074 | 35.80% |
| 20.14 | 4.40646 | 11.00% |
| 20.76 | 4.27452 | 25.90% |
| 21.49 | 4.13203 | 13.10% |
| 22.85 | 3.88916 | 10.50% |
| 23.50 | 3.78195 | 17.90% |
| 24.09 | 3.69144 | 10.80% |
| 24.46 | 3.63592 | 5.90% |
| 25.02 | 3.55605 | 5.90% |
| 25.82 | 3.44726 | 15.70% |
| 26.59 | 3.34968 | 60.60% |
| 27.30 | 3.26413 | 10.20% |
| 27.66 | 3.22297 | 7.30% |
| 28.28 | 3.15336 | 11.10% |
| 28.51 | 3.12856 | 13.60% |
| 29.67 | 3.00887 | 3.30% |
| 30.31 | 2.94688 | 3.90% |
| 30.75 | 2.90506 | 4.60% |
| 31.44 | 2.84307 | 9.10% |
| 32.75 | 2.73225 | 10.50% |
| 33.39 | 2.68143 | 9.00% |
| 34.40 | 2.60519 | 9.00% |
| 35.31 | 2.53958 | 4.20% |
| 35.97 | 2.49504 | 3.20% |
| 37.10 | 2.42147 | 4.60% |
| 38.02 | 2.36462 | 6.30% |
| 39.02 | 2.30673 | 1.80% |
| 39.83 | 2.26136 | 1.90% |

Example 5. Preparation of NMNH Calcium Salt Crystalline Form D 500 ml of NMNH calcium salt aqueous solution was stirred in a 20-30° C. oil bath, and 2 L of ethanol was slowly added dropwise, with the dropping time being more than 1 hour. After the addition was complete, stirring was continued for 1-2 hours, filtered, and dried at 30-40° C. to obtain 80.7 g of NMNH calcium salt crystals. The obtained crystals were crystalline form D, with a yield of 85.5% and a purity of 99.64%.

Figure 4:
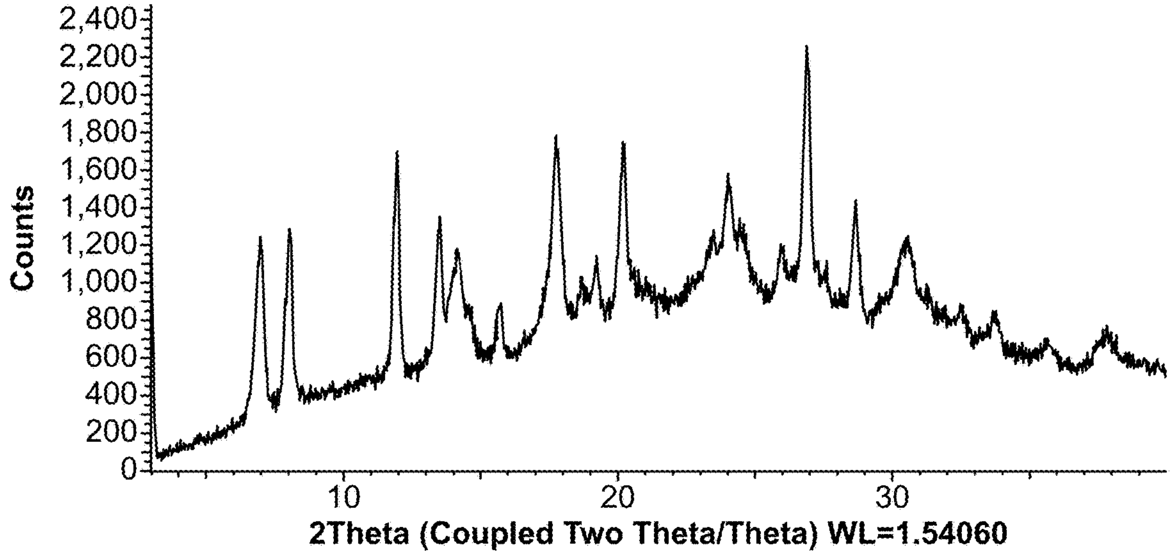
FIG. 4 shows an XRPD pattern of NMNH calcium salt crystalline form D.

The obtained solid was subjected to X-ray powder diffraction testing. The XRPD pattern of crystalline form C obtained was basically as shown in FIG. 4, and the diffraction angle data were basically as shown in Table 4 below, with an error range of ±0.2° for the 2θ values.

Figure 7:
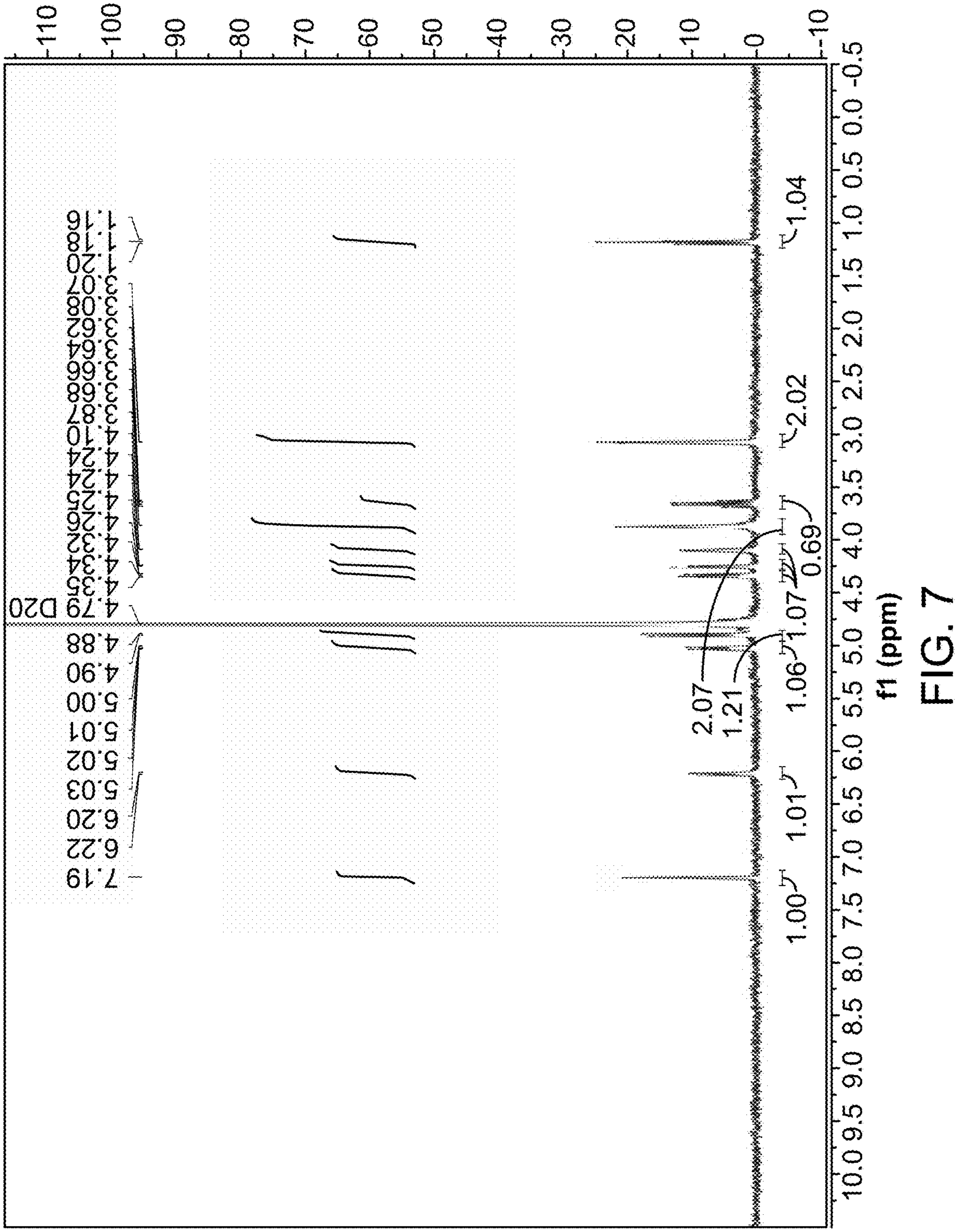
FIG. 7 shows a $^1$H NMR spectrum of NMNH calcium salt ethanol-hydrate crystalline form D.

The crystalline form D is an ethanol hydrate, with a water content of 18.4% wt. Its $^{1}H$ NMR spectrum is shown in FIG. 7, indicating that each molecule of NMNH calcium salt contains about 0.33 molecules of ethanol.

TABLE 4

| XRPD data of crystalline form D | | |
|---|---|---|
| 2θ (°) | d (Å) | Relative intensity |
| 6.96 | 12.68271 | 57.90% |
| 8.05 | 10.98098 | 64.80% |
| 11.95 | 7.39903 | 83.90% |
| 13.50 | 6.5555 | 55.10% |
| 14.15 | 6.25583 | 40.70% |
| 15.71 | 5.63829 | 19.30% |
| 17.78 | 4.98576 | 76.00% |
| 19.22 | 4.61411 | 22.10% |
| 20.23 | 4.38555 | 59.90% |
| 23.49 | 3.78437 | 26.30% |

TABLE 4-continued

| XRPD data of crystalline form D | | |
|---|---|---|
| 2θ (°) | d (Å) | Relative intensity |
| 24.04 | 3.69955 | 48.10% |
| 24.46 | 3.63676 | 29.40% |
| 26.05 | 3.41811 | 20.30% |
| 26.92 | 3.30879 | 100.00% |
| 28.69 | 3.10959 | 44.40% |
| 30.53 | 2.92623 | 32.30% |
| 33.76 | 2.65289 | 9.00% |

Example 6. Preparation of NMNH Calcium Salt Crystalline Form E 500 ml of NMNH calcium salt aqueous solution was stirred in a 20-30° C. oil bath, and 2 L of acetone was slowly added dropwise, with the dropping time being more than 1 hour. After the addition was complete, stirring was continued for 1-2 hours, filtered, and dried at 30-40° C. to obtain 80.8 g of NMNH calcium salt crystals. The obtained crystals were crystalline form E, with a yield of 85.6% and a purity of 99.60%.

Figure 5:
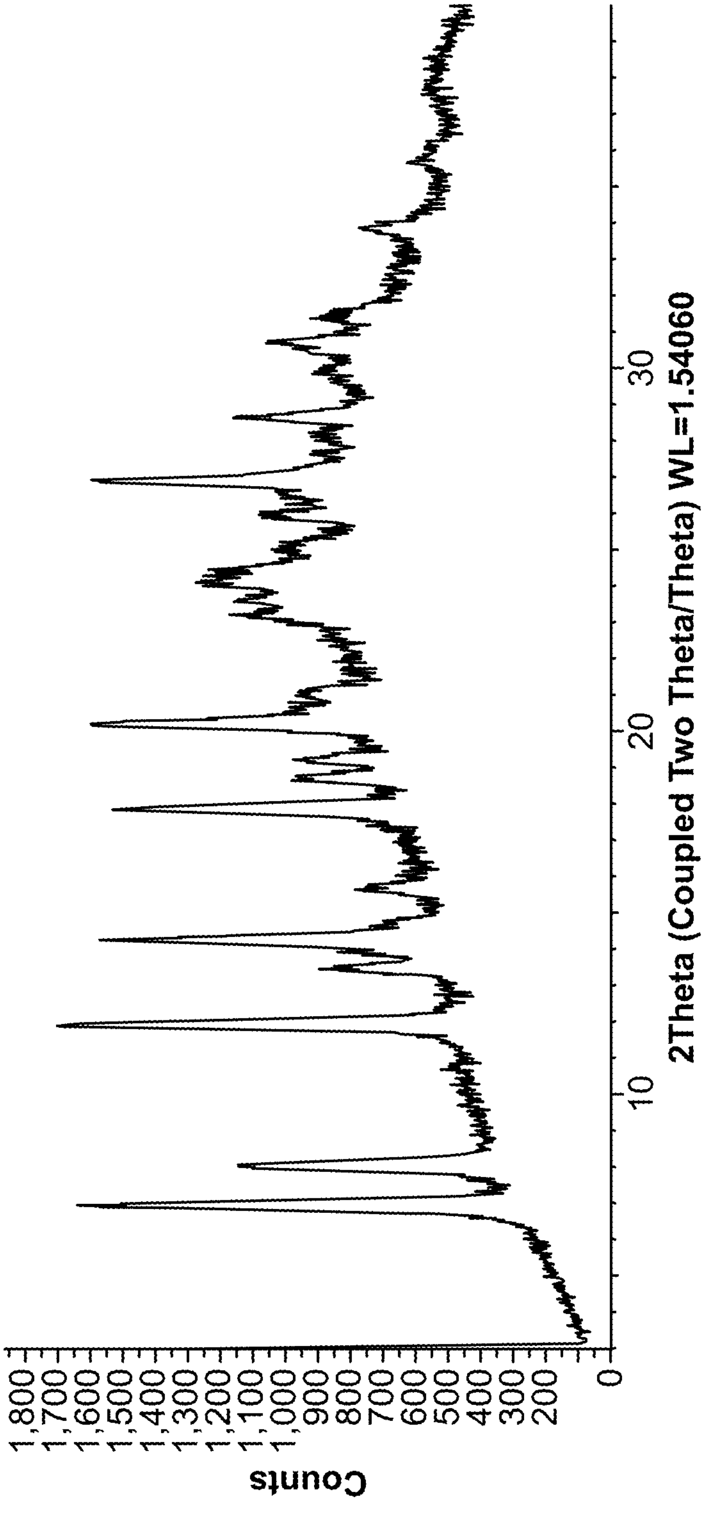
FIG. 5 shows an XRPD pattern of NMNH calcium salt crystalline form E.

The obtained solid was subjected to X-ray powder diffraction testing. The XRPD pattern of crystalline form C obtained was basically as shown in FIG. 5, and the diffraction angle data were basically as shown in Table 5 below, with an error range of ±0.2° for the 2θ values.

Figure 8:
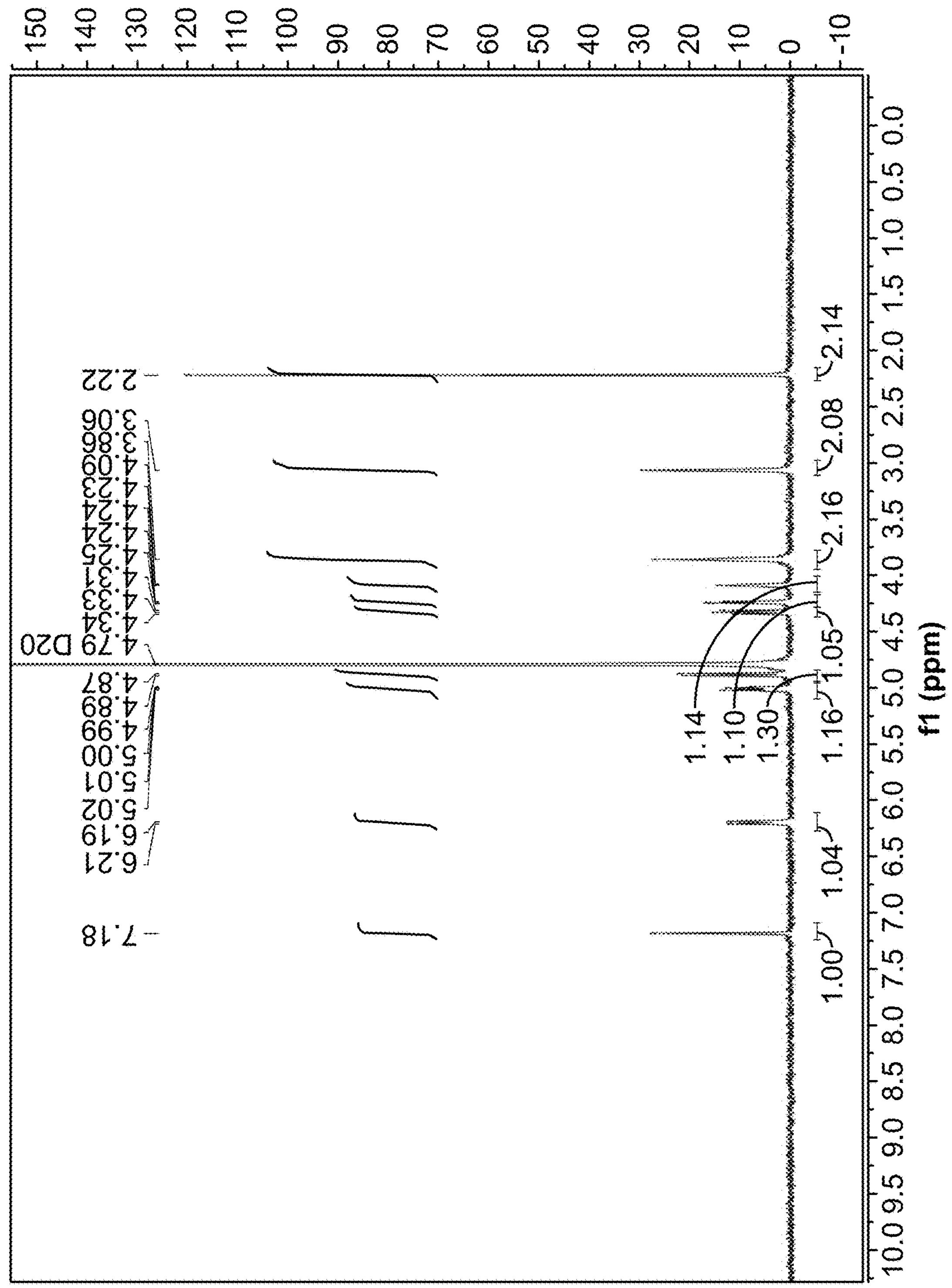
FIG. 8 shows a $^1$H NMR spectrum of NMNH calcium salt acetone-hydrate crystalline form E.

The crystalline form E is an acetone hydrate, with a water content of 20.3% wt. Its $^1$H NMR spectrum is shown in FIG. 8, indicating that each molecule of NMNH calcium salt contains about 0.33 molecules of acetone.

TABLE 5

| XRPD data of crystalline form E | | |
|---|---|---|
| 2θ (°) | d (Å) | Relative intensity |
| 6.93 | 12.74914 | 99.90% |
| 8.03 | 10.99837 | 63.00% |
| 11.91 | 7.42592 | 100.00% |
| 13.46 | 6.57313 | 34.30% |
| 14.24 | 6.21293 | 85.30% |
| 15.65 | 5.65952 | 20.50% |
| 17.85 | 4.96424 | 74.30% |
| 18.75 | 4.72936 | 24.30% |
| 19.22 | 4.61471 | 22.10% |
| 20.18 | 4.39593 | 69.00% |
| 24.12 | 3.68643 | 41.30% |

TABLE 5-continued

| XRPD data of crystalline form E | | |
|---|---|---|
| 2θ (°) | d (Å) | Relative intensity |
| 25.97 | 3.42829 | 24.60% |
| 26.91 | 3.31089 | 59.50% |
| 28.65 | 3.11299 | 31.70% |
| 30.69 | 2.91044 | 26.30% |
| 33.87 | 2.64479 | 18.00% |

Example 7. Stability and Hygroscopicity Comparison of NMNH Calcium Salt Crystalline Form A, Crystalline Form B, Crystalline Form C, Crystalline Form D, Crystalline Form E with NMNH Disodium Salt Crystalline Form A and Amorphous Solid The solid forms of NMNH calcium salt crystalline form A, crystalline form B, crystalline form C, crystalline form D, and crystalline form E were placed openly in a stability test chamber at 25° C. and 65% RH to evaluate their stability and hygroscopicity. The data obtained are shown in Table 6 and Table 7.

TABLE 6

Stability Comparison of NMNH Calcium Salt Crystalline Form A, Crystalline Form B, Crystalline Form C, Crystalline Form D, Crystalline Form E with NMNH Disodium Salt Crystalline Form A and Amorphous Solid (25° C., 65% RH)

| | Purity (HPLC, area %) | | | | | | |
|---|---|---|---|---|---|---|---|
| | NMNH disodium salt | | NMNH calcium salt | | | | |
| Time | Crystalline Form A | Amorphous Form | Crystalline Form A | Crystalline Form B | Crystalline Form C | Crystalline Form D | Crystalline Form E |
| 0 day | 99.33 | 99.30 (powder) | 99.83 | 99.75 | 99.78 | 99.64 | 99.60 |
| 1 day | 99.27 | 99.02 (oil) | / | / | / | / | / |
| 5 days | 99.01 | / | 99.82 | 99.75 | 99.78 | 99.64 | 99.60 |
| 60 days | / | / | 99.82 | 99.75 | 99.79 | 99.64 | 99.59 |

TABLE 7

Hygroscopicity Study of NMNH Calcium Salt Crystalline Form A, Crystalline Form B, Crystalline Form C, Crystalline Form D, and Crystalline Form E Solids (25° C., 65% RH)

| | Water content of NMNH calcium salt crystalline form (KF) | | | | |
|---|---|---|---|---|---|
| Time | Crystalline Form A | Crystalline Form B | Crystalline Form C | Crystalline Form D | Crystalline Form E |
| 0 day | 9.2% | 13.3% | 9.5% | 18.4% | 20.3% |
| 5 days | 9.2% | 13.2% | 9.5% | 18.4% | 20.3% |
| 60 days | 9.0% | 12.9% | 9.3% | 18.3% | 20.0% |

After being placed for 60 days, the purity and water content of NMNH calcium salt crystalline form A, crystalline form B, crystalline form C, crystalline form D, and crystalline form E solids showed almost no change, indicating that NMNH calcium salt crystalline form A, crystalline form B, crystalline form C, crystalline form D, and crystalline form E solids can be placed openly under conditions of 25° C. and 65% RH for no less than 60 days with continuously stable purity and water content.

According to WO2023160405 (A1), when NMNH disodium salt is stored in the air, both crystalline forms B and C absorb water and transform into crystalline form A. After saturation with water, the water content of crystalline form A is 19%-30% (high water content), and the purity drops from 99.33% to 99.01% after 5 days. The amorphous solid of NMNH disodium salt is more unstable in the air. After 1 day of storage, it absorbs water from powder to oil, and the purity drops from 99.30% to 99.02%.

It can be seen that both the crystalline and amorphous forms of NMNH disodium salt are unstable and easily absorb moisture, which is extremely unfavorable for storage, cannot meet commercial shelf life requirements, and is difficult to promote for market launch. The stability and moisture resistance of NMNH calcium salt crystalline form A, crystalline form B, crystalline form C, crystalline form D, and crystalline form E solids are significantly improved, facilitating long-term continuous and stable storage, and are conducive to market promotion.

All documents mentioned in the present invention are cited as references in the present application, just as if each document was cited as reference individually. In addition, it should be understood that after reading the above teachings of the present invention, a person skilled in the art can make various changes or modifications to the present invention, and these equivalent forms also fall within the scope defined by the appended claims of the present application.

The invention claimed is:

1. A crystalline calcium salt of a reduced ß-nicotinamide mononucleotide, wherein the crystalline calcium salt has a structure of Formula (I),

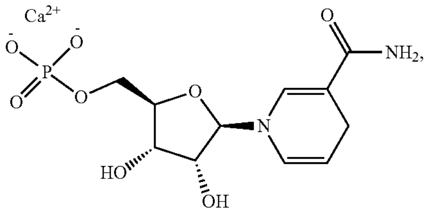

(I)

and wherein the crystalline calcium salt has an X-ray powder diffraction (XRPD) pattern having peaks at one of the following:

(a) at least three 2θ values selected from the group consisting of: 6.9°±0.2°, 9.5°±0.2°, 12.6°±0.2°, 15.6°±0.2°, 17.9°±0.2°, 21.0°±0.2°, 21.8°±0.2°, and 25.4°±0.2°;

(b) at least three 2θ values selected from the group consisting of: 6.5°±0.2°, 8.1°±0.2°, 11.9°±0.2°, 13.1°±0.2°, 17.6°±0.2°, 21.4°±0.2°, 23.7°±0.2°, and 26.9°±0.2°;

(c) at least three 2θ values selected from the group consisting of: 6.2°±0.2°, 9.7°±0.2°, 12.4°±0.2°, 16.1°±0.2°, 17.1°±0.2°, 18.7°±0.2°, 20.8°±0.2°, and 26.6°±0.2°;

(d) at least three 2θ values selected from the group consisting of: 7.0°±0.2°, 8.0°±0.2°, 12.0°±0.2°, 17.8°±0.2°, 20.2°±0.2°, 26.9°±0.2°; or (e) at least three 2θ values selected from the group consisting of: 6.9°±0.2°, 8.0°±0.2°, 11.9°±0.2°, 17.8°±0.2°, 20.2°±0.2°, 26.9°±0.2°.

2. The crystalline calcium salt of claim 1, wherein the crystalline calcium salt has an X-ray powder diffraction (XRPD) pattern having peaks at at least three 2θ values selected from the group consisting of: 6.9°±0.2°, 9.5°±0.2°, 12.6°±0.2°, 15.6°±0.2°, 17.9°±0.2°, 21.0°±0.2°, 21.8°±0.2°, and 25.4°±0.2°.

3. The crystalline calcium salt of claim 1, wherein the crystalline calcium salt has an XRPD pattern having peaks at at least six 2θ values selected from the group consisting of: 6.9°±0.2°, 9.5°±0.2°, 12.6°±0.2°, 13.9°±0.2°, 14.4°±0.2°, 15.6°±0.2°, 16.7°±0.2°, 17.2°±0.2°, 17.9°±0.2°, 18.8°±0.2°, 21.0°±0.2°, 21.8°±0.2°, 23.1°±0.2°, 25.4°±0.2°, 26.5°±0.2°, 27.3°±0.2°, 28.1°±0.2°, 31.5°±0.2°, 32.8°±0.2°, and 35.6°±0.2°.

4. The crystalline calcium salt of claim 1, wherein the crystalline calcium salt has an XRPD pattern having peaks at at least three 2θ values selected from the group consisting of: 6.5°±0.2°, 8.1°±0.2°, 11.9°±0.2°, 13.1°±0.2°, 17.6°±0.2°, 21.4°±0.2°, 23.7°±0.2°, and 26.9°±0.2°.

5. The crystalline calcium salt of claim 1, wherein the crystalline calcium salt has an XRPD pattern having peaks at at least six 2θ values selected from the group consisting of: 6.5°±0.2°, 8.1°±0.2°, 11.9°±0.2°, 13.1°±0.2°, 13.5°±0.2°, 14.5°±0.2°, 17.6°±0.2°, 18.0°±0.2°, 18.9°±0.2°, 19.4°±0.2°, 19.7°±0.2°, 20.3°±0.2°, 21.4°±0.2°, 23.7°±0.2°, 24.3°±0.2°, 25.1°±0.2°, 26.4°±0.2°, 26.9°±0.2°, 27.5°±0.2°, 28.7°±0.2°, 29.3°±0.2°, 30.5°±0.2°, 30.9°±0.2°, 31.6°±0.2°, 32.4°±0.2°, 32.9°±0.2°, 34.2°±0.2°, 35.0°±0.2°, 35.4°±0.2°, 36.7°±0.2°, 37.5°±0.2°, 37.9°±0.2°, 38.2°±0.2°, 38.9°±0.2°, and 40.2°±0.2°.

6. The crystalline calcium salt of claim 1, wherein the crystalline calcium salt has an XRPD pattern having peaks at at least three 2θ values selected from the group consisting of: 6.2°±0.2°, 9.7°±0.2°, 12.4°±0.2°, 16.1°±0.2°, 17.1°±0.2°, 18.7°±0.2°, 20.8°±0.2°, and 26.6°±0.2°.

7. The crystalline calcium salt of claim 1, wherein the crystalline calcium salt has an XRPD pattern having peaks at at least six 2θ values selected from the group consisting of: 6.2°±0.2°, 6.8°±0.2°, 9.7°±0.2°, 11.8°±0.2°, 12.4°±0.2°, 14.2°±0.2°, 15.5°±0.2°, 16.1°±0.2°, 17.1°±0.2°, 17.9°±0.2°, 18.7°±0.2°, 20.1°±0.2°, 20.8°±0.2°, 21.5°±0.2°, 22.9°±0.2°, 23.5°±0.2°, 24.1°±0.2°, 24.5°±0.2°, 25.0°±0.2°, 25.8°±0.2°, 26.6°±0.2°, 27.3°±0.2°, 27.7°±0.2°, 28.3°±0.2°, 28.5°±0.2°, 29.7°±0.2°, 30.3°±0.2°, 30.8°±0.2°, 31.4°±0.2°, 32.8°±0.2°, 33.4°±0.2°, 34.4°±0.2°, 35.3°±0.2°, 36.0°±0.2°, 37.1°±0.2°, 38.0°±0.2°, 39.0°±0.2°, and 39.8°±0.2°.

8. The crystalline calcium salt of claim 1, wherein the crystalline calcium salt has an XRPD pattern having peaks at at least three 2θ values selected from the group consisting of: 7.0°±0.2°, 8.0°±0.2°, 12.0°±0.2°, 17.8°±0.2°, 20.2°±0.2°, 26.9°±0.2°.

9. The crystalline calcium salt of claim 1, wherein the crystalline calcium salt has an XRPD pattern having peaks at at least three 2θ values selected from the group consisting of: 7.0°±0.2°, 8.0°±0.2°, 12.0°±0.2°, 13.5°±0.2°, 14.2°±0.2°, 15.7°±0.2°, 17.8°±0.2°, 19.2°±0.2°, 20.2°±0.2°, 23.5°±0.2°, 24.0°±0.2°, 24.5°±0.2°, 26.1°±0.2°, 26.9°±0.2°, 28.7°±0.2°, 30.5°±0.2°, 33.8°±0.2°.

10. The crystalline calcium salt of claim 1, wherein the crystalline calcium salt has an XRPD pattern having peaks at at least three 2θ values selected from the group consisting of: 6.9°±0.2°, 8.0°±0.2°, 11.9°±0.2°, 17.8°±0.2°, 20.2°±0.2°, 26.9°±0.2°.

11. The crystalline calcium salt of claim 1, wherein the crystalline calcium salt has an XRPD pattern having peaks at at least three 2θ values selected from the group consisting of: 6.9°±0.2°, 8.0°±0.2°, 11.9°±0.2°, 13.5°±0.2°, 14.2°±0.2°, 15.7°±0.2°, 17.8°±0.2°, 18.8°±0.2°, 19.2°±0.2°, 20.2°±0.2°, 24.1°±0.2°, 26.0°±0.2°, 26.9°±0.2°, 28.7°±0.2°, 30.7°±0.2°, 33.9°±0.2°.

12. A composition comprising:

the crystalline calcium salt of claim 1; and at least one excipient or carrier selected from the group consisting of a pharmaceutically acceptable excipient or carrier, a health product acceptable excipient or carrier, a cosmetically acceptable excipient or carrier, and a food acceptable excipient or carrier.

13. A crystalline calcium salt of a reduced β-nicotinamide mononucleotide, wherein the crystalline calcium salt has a structure of Formula (I), (I)

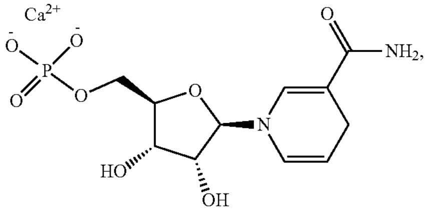

wherein the crystalline calcium salt comprises a crystalline form selected from the group consisting of crystalline form A, crystalline form B, crystalline form C, crystalline form D, and crystalline form E, wherein the crystalline form A exhibits an XRPD pattern of FIG. 1;

the crystalline form B exhibits an XRPD pattern of FIG. 2;

the crystalline form C exhibits an XRPD pattern of FIG. 3;

the crystalline form D exhibits an XRPD pattern of FIG. 4; and the crystalline form E exhibits an XRPD pattern of FIG. 5.

14. The crystalline calcium salt of claim 13, wherein:

the crystalline form A is a hydrate selected from the group consisting of monohydrate, dihydrate, trihydrate, and combinations thereof;

the crystalline form B is a hydrate selected from the group consisting of monohydrate, dihydrate, trihydrate, tetrahydrate, pentahydrate, and combinations thereof;

the crystalline form C is a hydrate selected from the group consisting of monohydrate, dihydrate, trihydrate, and combinations thereof;

the crystalline form D is a hydrate selected from the group consisting of trihydrate, tetrahydrate, pentahydrate, hexahydrate, and combinations thereof; and the crystalline form E is a hydrate selected from the group consisting of trihydrate, tetrahydrate, pentahydrate, hexahydrate, and combinations thereof.

15. The crystalline calcium salt of claim 13, wherein:

the crystalline form A has a water content of 4% to 13% by weight;

the crystalline form B has a water content of 4% to 20% by weight;

the crystalline form C has a water content of 4% to 13% by weight;

the crystalline form D has a water content of 16% to 23% by weight; and the crystalline form E has a water content of 16% to 23% by weight.

16. The crystalline calcium salt of claim 13, wherein:

the crystalline form D is a hydrate further comprising water and ethanol, and a molar ratio of the crystalline calcium salt of Formula (I) to ethanol present in the crystalline form D is 4:1 to 1:1; and the crystalline form E is a hydrate further comprising water and acetone, and a molar ratio of the crystalline calcium salt of Formula (I) to acetone present in the crystalline form E is 4:1 to 1:1.

17. A method for preparing the crystalline calcium salt of a reduced β-nicotinamide mononucleotide of claim 13, wherein the method comprises:

a) providing a solution of a reduced β-nicotinamide mononucleotide calcium salt in a first solvent or a first mixture thereof;

b) adding the solution obtained in step a) into a second solvent thereby forming a second mixture comprising the crystalline calcium salt of the reduced β-nicotinamide mononucleotide in the form of a precipitate; and c) separating the crystalline calcium salt from the second mixture; and e) drying the crystalline calcium salt.

18. The method of claim 17, wherein the first solvent and the second solvent are each independently selected from the group consisting of water, acetonitrile, tetrahydrofuran, methyl tert-butyl ether, 2-methyltetrahydrofuran, dichloromethane, N,N-dimethylformamide, N,N-dimethylacetamide, N,N-diethylformamide, dimethyl sulfoxide, ethyl acetate, isopropyl acetate, acetone, methyl ethyl ketone, methanol, ethanol, n-propanol, isopropanol, and combinations thereof.

19. The method of claim 17, wherein, when the first solvent comprises water, and when the second solvent is selected from the group consisting of water, methanol, ethanol, n-propanol, isopropanol, acetone, acetonitrile, tetrahydrofuran, and combinations thereof, the crystalline calcium salt is the crystalline form A.

20. The method of claim 19, wherein:

the solution obtained in step a) is added into the second solvent at 40-50° C.; and after step c), the crystalline calcium salt is dried at 40-50° C. to provide the crystalline form A of the reduced B-nicotinamide mononucleotide calcium salt.

21. The method of claim 17, wherein, when the first solvent comprises water, and when the second solvent is selected from the group consisting of water, methanol, and combinations thereof, the crystalline calcium salt is the crystalline form B.

22. The method of claim 21, wherein:

the solution obtained in step a) is added into the second solvent at 20-30° C.; and after step c), the crystalline calcium salt is dried at 20-30° C. to provide the crystalline form B of the reduced β-nicotinamide mononucleotide calcium salt.

23. The method of claim 17, wherein, when the first solvent comprises water, and when the second solvent is selected from the group consisting of water, methanol, and combinations thereof, the crystalline calcium salt is the crystalline form C.

24. The method of claim 23, wherein:

the solution obtained in step a) is added into the second solvent at 20-30° C.; and after step c), the crystalline calcium salt is dried at 40-50° C. to provide the crystalline form C of the reduced β-nicotinamide mononucleotide calcium salt.

25. The method of claim 17, wherein, when the first solvent comprises water, and when the second solvent is selected from the group consisting of water, ethanol, and combinations thereof, the crystalline calcium salt is the crystalline form D.

26. The method of claim 25, wherein:

the solution obtained in step a) is added into the second solvent at 20-30° C.; and after step c), the crystalline calcium salt is dried at 30-40° C. to provide the crystalline form D of the reduced β-nicotinamide mononucleotide calcium salt.

27. The method of claim 17, wherein, when the first solvent comprises water, and when the second solvent is selected from the group consisting of water, acetone, and combinations thereof, the crystalline calcium salt is the crystalline form E.

28. The method of claim 27, wherein:

the solution obtained in step a) is added into the second solvent at 20-30° C.; and after step c), the crystalline calcium salt is dried at 30-40° C. to provide the crystalline form E of the reduced β-nicotinamide mononucleotide calcium salt.

* * * * *